(12) United States Patent
Gearheart et al.

(10) Patent No.: US 11,147,618 B2
(45) Date of Patent: Oct. 19, 2021

(54) ELECTROSURGICAL UNIT AND SYSTEM

(71) Applicant: MEDTRONIC ADVANCED ENERGY LLC., Minneapolis, MN (US)

(72) Inventors: John Gearheart, Minneapolis, MN (US); David Hubelbank, Litchfield, NH (US); Jesse Smith, Minneapolis, MN (US); Vini Podany, New Fairfield, CT (US)

(73) Assignee: MEDTRONIC ADVANCED ENERGY LLC, Minneapolis, MN (US)

( * ) Notice: Subject to any disclaimer, the term of this patent is extended or adjusted under 35 U.S.C. 154(b) by 512 days.

(21) Appl. No.: 15/852,890

(22) Filed: Dec. 22, 2017

(65) Prior Publication Data

US 2018/0193092 A1    Jul. 12, 2018

Related U.S. Application Data

(60) Provisional application No. 62/445,034, filed on Jan. 11, 2017.

(51) Int. Cl.
*A61B 18/16* (2006.01)
*A61B 18/12* (2006.01)
(Continued)

(52) U.S. Cl.
CPC .......... *A61B 18/16* (2013.01); *A61B 18/1206* (2013.01); *A61B 18/1482* (2013.01); *A61B 2018/0063* (2013.01); *A61B 2018/00642* (2013.01); *A61B 2018/00666* (2013.01); *A61B 2018/00708* (2013.01); *A61B 2018/00827* (2013.01); *A61B 2018/00833* (2013.01); *A61B 2018/00875* (2013.01); *A61B 2018/00892* (2013.01); *A61B 2018/00898* (2013.01);
(Continued)

(58) Field of Classification Search
CPC ...................... A61B 2018/00875; A61B 18/16
See application file for complete search history.

(56) References Cited

U.S. PATENT DOCUMENTS 5,769,880 A    6/1998  Truckai et al.
5,797,903 A    8/1998  Swanson et al.
(Continued)

FOREIGN PATENT DOCUMENTS

WO    9525471    9/1995

OTHER PUBLICATIONS

International Searching Authority, Search Report and Written Opinion, dated Sep. 17, 2018, 13 pages.

*Primary Examiner* — Michael F Peffley
*Assistant Examiner* — Bo Ouyang
(74) *Attorney, Agent, or Firm* — Dicke, Billig & Czaja, PLLC

(57) ABSTRACT

Systems, such as an electrosurgical unit, and method for use with an active electrode and a plurality of return electrodes are disclosure. An electrosurgical treatment is provided to tissue via the active electrode at a treatment site and a first return electrode of the plurality of return electrodes at the treatment site. An impedance measurement is received or determined of an impedance in the tissue between the active electrode at the treatment site and a second return electrode of the plurality of return electrodes at a site remote from the treatment site.

50 Claims, 6 Drawing Sheets

(51) Int. Cl.
*A61B 18/00* (2006.01)
*A61B 18/14* (2006.01)

(52) U.S. Cl.
CPC . *A61B 2018/126* (2013.01); *A61B 2018/1472* (2013.01); *A61B 2018/165* (2013.01); *A61B 2018/167* (2013.01); *A61B 2218/002* (2013.01)

(56) References Cited

U.S. PATENT DOCUMENTS

| | | |
|---|---|---|
| 6,508,815 B1 | 1/2003 | Strul et al. |
| 8,663,214 B2 | 3/2014 | Weinberg et al. |
| 2008/0097139 A1* | 4/2008 | Clerc ................ A61B 18/1482 600/7 |
| 2008/0287948 A1 | 11/2008 | Newton et al. |
| 2010/0179538 A1* | 7/2010 | Podhajsky ......... A61B 18/1206 606/35 |
| 2015/0105701 A1 | 4/2015 | Mayer et al. |
| 2015/0320481 A1* | 11/2015 | Cosman, Jr. ........... A61B 34/10 606/35 |
| 2016/0184011 A1* | 6/2016 | Krishnan ........... A61B 18/1492 606/14 |
| 2016/0310203 A1 | 10/2016 | Gaspredes et al. |
| 2016/0331446 A1* | 11/2016 | Martin ............... A61B 18/1492 |

\* cited by examiner

ELECTROSURGICAL UNIT AND SYSTEM

CROSS REFERENCE TO RELATED APPLICATION

This Non-Provisional Utility Application claims benefit to U.S. Provisional Application No. 62/445,034, filed Jan. 11, 2017, titled "ELECTROSURGICAL UNIT AND SYSTEM," the entirety of which incorporated herein by reference.

BACKGROUND

This disclosure relates generally to the field of medical devices, systems and methods for use in surgical procedures. More specifically, this disclosure relates to electrosurgical devices, units, systems and methods that can provide for cutting, coagulation, hemostasis, or sealing of bodily tissues including bone with an electrosurgical device.

Electrosurgery includes such techniques as cutting, coagulation, hemostasis, and/or sealing of tissues with the aid of electrodes energized with a suitable power source. Typical electrosurgical devices apply an electrical potential difference or signal between an active electrode and a return electrode on a patient's grounded body in a monopolar arrangement or between an active electrode and a return electrode on the device in bipolar arrangement to deliver electrical energy to the area where tissue is to be affected. The electrosurgical devices are typically held by the surgeon and connected to the power source, such as an electrosurgical unit having a power generator, via cabling.

Electrosurgical devices pass electrical energy through tissue between the electrodes to provide coagulation to control bleeding and hemostasis to seal tissue. Electrosurgical devices can also cut tissue through the use of plasma formed on the electrode. Tissue that contacts the plasma experiences a rapid vaporization of cellular fluid to produce a cutting effect. Typically, cutting and coagulation are often performed with electrodes in the monopolar arrangement while hemostasis is performed with electrodes in the bipolar arrangement. Historically, two distinct electrosurgical devices, one monopolar and the other bipolar, were used to perform different functions in surgery, such as tissue cutting and coagulating and tissue sealing. Some electrosurgical devices capable of performing multiple techniques such as cutting and coagulating tissue or cutting, coagulating, and sealing tissue, including fluid-assisted sealing of tissue, have been developed.

Dry-tip electrosurgical devices can adversely affect tissue and surgical procedures by desiccating or perforating tissue, causing tissue to stick to the electrodes, burning or charring tissue, and generating smoke at the surgical site. More recently, fluid-assisted electrosurgical devices have been developed that use saline to inhibit such undesirable effects as well as to control the temperature of the tissue being treated and to electrically couple the device to the tissue. Fluid-assisted electrosurgical devices have been developed which, when used in conjunction with an electrically conductive fluid such as saline, may be moved along a tissue surface without cutting the tissue to seal tissue to inhibit blood and other fluid loss during surgery.

Fluid-assisted electrosurgical devices apply radiofrequency (RF) electrical energy and electrically conductive fluid to provide for sealing of soft tissues and bone in applications of orthopedics (such as total hip arthroplasty, or THA, and total knee arthroplasty, or TKA), spinal oncology, neurosurgery, thoracic surgery, and cardiac implantable electronic devices as well as others such as general surgery within the human body. The combination of RF energy and the electrically conductive fluid permits the electrosurgical device to operate at approximately 100 degrees Celsius, which is nearly 200 degrees Celsius less than traditional electrosurgical devices. Typically, hemostasis is performed with fluid-assisted devices having electrodes in the bipolar arrangement that are referred to as bipolar sealers. By controlling bleeding, bipolar sealers have been demonstrated to reduce the incidence of hematoma and transfusions, help maintain hemoglobin levels, and reduce surgical time in a number of procedures, and may reduce the use of hemostatic agents.

Electrical signals can be applied to the electrodes either as a train of high frequency pulses or as a continuous signal typically in the radiofrequency (RF) range to perform the different techniques. The signals can include a variable set of parameters, such as power or voltage level, waveform parameters such as frequency, pulse duration, duty cycle, and other signal parameters that may be particularly apt or preferred for a given technique. For example, a surgeon could cut tissue using a first RF signal having a set of parameters to form plasma and control bleeding using a second RF signal having another set of parameters more preferred for coagulation. The surgeon could also use electrodes in a bipolar arrangement or a bipolar electrosurgical device for hemostatic sealing of the tissue that would employ additional RF signals having another set of parameters.

Electrosurgical units that deliver power to the electrosurgical devices also control the power to provide an effective treatment. For example, electrosurgical units can measure the difference in voltages between the active electrode and the return electrode and divide this difference by the measured current between the electrodes to calculate the electrical impedance of the tissue. The amount of tissue impedance can be related to the amount of energy delivered to a treatment site. Impedance of tissue will increase with thermal delivery until the impedance reaches a plateau, at which point additional thermal delivery will no longer effectively treat the tissue as intended. As electrical resistance of tissue located between two electrodes increases, the electrosurgical current will seek a new path from the active electrode to the return through tissue with a lower resistance, thereby spreading the delivery of thermal energy. Electrosurgical units can measure tissue impedance and selectively adjust the power output, such as reduce power or cease power, to the electrosurgical device to avoid excessive or unintended treatment or thermal delivery to the tissue.

In some circumstances of bipolar treatment, however, tissue impedance is difficult to detect. For example, the presence of a conductive fluid such as saline in the area of thermal delivery during hemostasis may add a parallel electrical load to the tissue between the active electrode and the return electrode. The conductive fluid may provide a less resistive path for electrical energy between the electrodes than tissue. Further, the conductive fluid, unlike tissue, generally provides a constant impedance when subjected to electrical energy. The parallel load in the presence of tissue can affect the impedance measurement in the form of electrical noise that can adversely affect the ability of the electrosurgical unit to determine when or whether to adjust power.

SUMMARY

This summary is provided to introduce a selection of concepts in a simplified form that are further described below in the Detailed Description.

Impedance of tissue at the treatment site will increase with thermal delivery from an electrosurgical device until the impedance reaches a plateau, at which point thermal delivery will no longer effectively treat the tissue. At this point, an electrosurgical unit can adjust power, such as cut power or reduce power, in the signal to the active electrode, for example to cease treatment. In some circumstances of bipolar treatment, however, the impedance and the impedance plateau are difficult to detect with a bipolar electrosurgical device and typical electrosurgical units. For example, the presence of a conductive fluid such as saline in the area of thermal delivery during hemostasis may add a parallel electrical load to the tissue between the active electrode and the return electrode of the bipolar electrosurgical device.

The present disclosure relates to a method and system that may improve the ability to detect thermal effect via tissue impedance particularly in the bipolar treatment of tissue with the presence of fluid. An electrosurgical device in a bipolar configuration, which can disperse a fluid, is coupled to an electrosurgical unit. The electrosurgical device includes an active electrode and first return electrode that is configured to provide electrosurgical treatment of tissue at the tissue treatment site. A second return electrode, such as a pad dispersive electrode used in monopolar treatment of tissue or other return electrode, is also coupled to the electrosurgical unit to and to the tissue at a site remote from the treatment site. In one example, the first return electrode can be operably coupled to the second return electrode provide the voltage of the first return electrode. The voltage difference between the active electrode and the second return electrode as well as a current from the second return electrode are measured to determine tissue impedance. The impedance of the tissue between the active electrode and the first return electrode at the tissue treatment site may or may not be measured. Changes in the tissue impedance between the active electrode and the second return electrode can be used to detect thermal effect, such as an impedance plateau without the associated noise or issues introduced with the conductive fluid at the treatment site.

In one aspect, the present disclosure relates to method for use with an active electrode and a plurality of return electrodes. For example, the present disclosure relates to a method for use with electrosurgical device having an active electrode and a first return electrode to provide a bipolar treatment to tissue at a treatment site and to remote electrode disposed on the tissue at a remote site remote from the treatment site. An electrosurgical treatment is provided to tissue via the active electrode at a treatment site and a first return electrode of the plurality of return electrodes at the treatment site. An impedance measurement is received or determined of an impedance in the tissue between the active electrode at the treatment site and a second return electrode of the plurality of return electrodes at a site remote from the treatment site. The treatment can be adjusted based on the impedance measurement. In one example, the method is implemented as a non-transitory computer readable medium to store computer executable instructions to control a processor. For instance, the method is implemented with an electrosurgical unit such as an electrosurgical generator.

In one example, a first impedance measurement is received of an impedance in the tissue between the active electrode at the treatment site and the first return electrode at the treatment site. A second impedance measurement is received of an impedance in the tissue between the active electrode at the treatment site and a second return electrode of the plurality of return electrodes at a site remote from the treatment site. The treatment can be adjusted based on a comparison of the first impedance measurement with the second impedance measurement An electrosurgical unit can include a radio-frequency (RF) circuit, a detection circuit, a processor or controller, and various connections to electrodes configured to provide treatment and take measurements of electrical signals in tissue at a treatment site and at a remote site. For example, the RF circuit is operably coupled to an output having an active electrode connection and a first return connection in which the RF circuit configured to provide a bipolar operation to via the active electrode connection. The detection circuit configured to be operably coupled to the active electrode connection and the first return electrode connection, the detection circuit further configure to be operably coupled to a second return electrode connection. The processor operably coupled to the detection circuit and configured to detect a potential difference between the active electrode connection and the second return electrode connection and a current in the second return electrode connection, and to determine an impedance measurement based on the potential difference and the current during bipolar operation.

DETAILED DESCRIPTION

Figure 1:
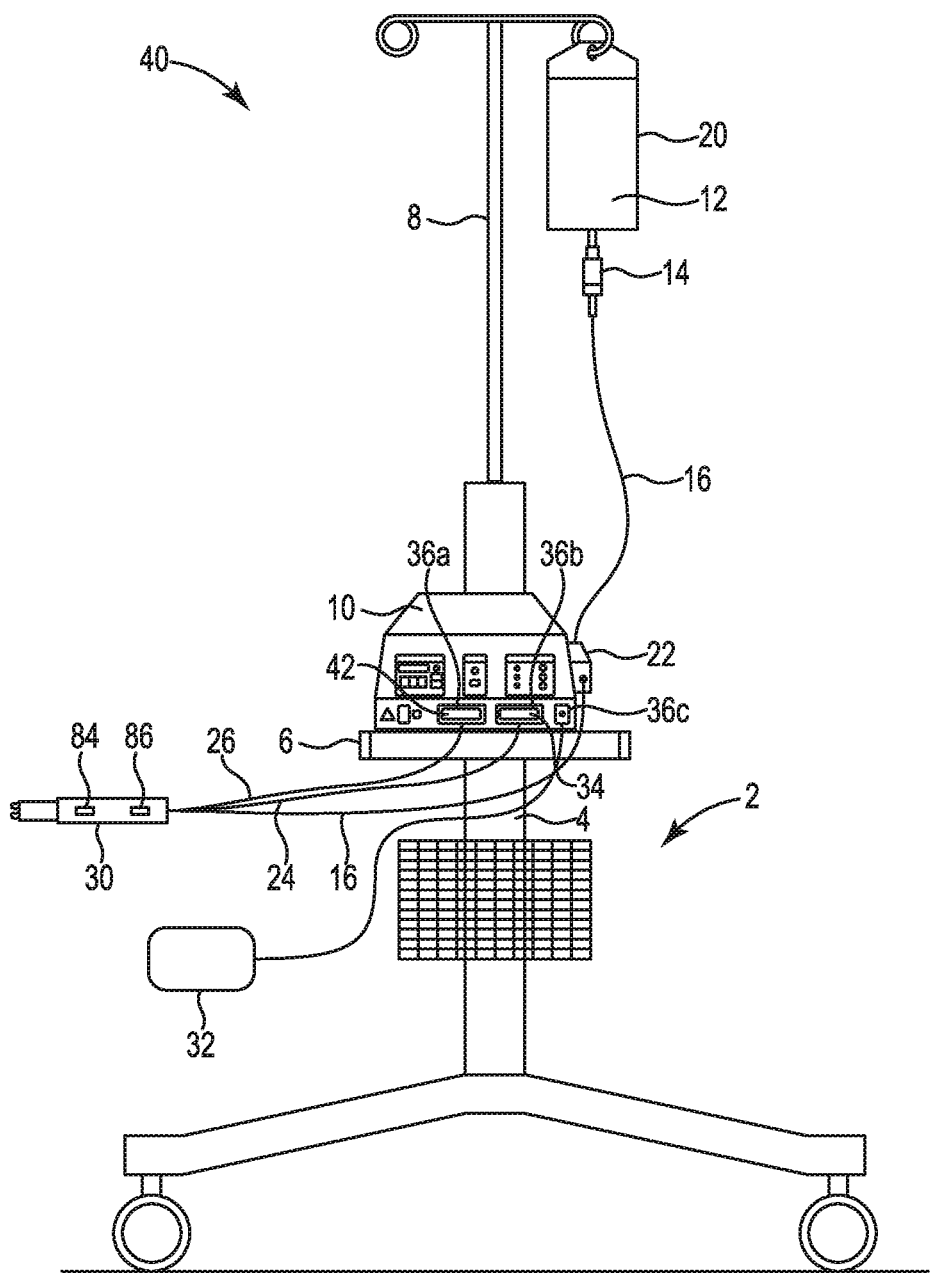
FIG. 1 is a front view illustrating an embodiment of an electrosurgical system according to the present disclosure including an example electrosurgical unit in combination with a fluid source and example handheld electrosurgical device.

Throughout the description, like reference numerals and letters indicate corresponding structure throughout the several views. Also, any particular features(s) of a particular exemplary embodiment may be equally applied to any other exemplary embodiment(s) of this specification as suitable. That is, features between the various exemplary embodiments described herein are interchangeable as suitable and may not be exclusive. From the specification, it should be clear that the terms "distal" and "proximal" are made in reference to a user of the device.

FIG. 1 illustrates a front view of one example of a system 40 that includes an electrosurgical unit 10 in combination with an example handheld electrosurgical device 30. The device 30, in one example, can be configurable for use in a bipolar mode. An additional monopolar device, not shown, may also be used in combination with the electrosurgical unit 10 as part of system 40. In another example, the device 30 is a multipurpose device configurable for use in cutting and sealing including electrocautery and coagulation in a monopolar mode using a monopolar electrode and configurable to provide hemostatic sealing of tissue including bone with a fluid in a bipolar mode using at least a second monopolar electrode in combination with a fluid source 20, or for other electrical surgical procedures.

The system 40 can be carried on a movable cart 2 having a support member 4 comprising a hollow cylindrical post which includes a platform 6 comprising a pedestal table to provide a flat, stable surface for location of the electrosurgical unit 10. Cart 2 can include a pole 8 having a height that can be adjusted by sliding the pole 8 up and down and secured in position with a set screw. The pole can include a cross support with loops at the end to form a hook. Fluid source 20 can be supported at the top of pole 8 via the hook. The movable cart 2 and its features are provided for illustration as an example.

Fluid source 20 may comprise a bag of fluid from which fluid 12 may flow through a drip chamber 14, to delivery tubing 16 and to handheld electrosurgical device 30. In one example, the fluid 12 includes saline and can include physiologic saline such as sodium chloride (NaCl) 0.9% weight/volume solution. Saline is an electrically conductive fluid, and other suitable electrically conductive fluids can be used. In other examples, the fluid may include a nonconductive fluid, such as deionized water, which may still provide advantages over using no fluid and may support cooling of portions of electrosurgical device 30 and tissue or reducing the occurrence of tissue sticking to the electrosurgical device 30.

The fluid delivery tubing 16 in the example passes through pump 22 to convey fluid to the electrosurgical device 30 and control fluid flow. Pump 22 in one example is a peristaltic pump such as a rotary peristaltic pump or a linear peristaltic pump. A peristaltic pump can convey the fluid through the delivery tubing 16 by way of intermittent forces placed on the external surface of the delivery tubing. Peristaltic pumps are often applied during use of the electrosurgical device 30 because the mechanical elements of the pump places forces on the external surface of the delivery tubing and do not come into direct contact with the fluid, which can reduce the likelihood of fluid contamination. Other examples of system 40 might not include a pump, and fluid can be is provided to the electrosurgical device 30 via gravity.

The example electrosurgical unit 10 is configured to provide bipolar or both monopolar and bipolar radio-frequency (RF) power output to a specified electrosurgical instrument such as electrosurgical device 30. In one example, the electrosurgical unit 10 can be used for delivery of RF energy to instruments indicated for cutting and coagulation of soft tissue and for delivery of RF energy concurrent with fluid to instruments indicated for hemostatic sealing and coagulation of soft tissue and bone. In one example, the electrosurgical unit 10 is capable of simultaneously powering specified monopolar and bipolar electrosurgical instruments but may include a lock out feature preventing both monopolar and bipolar output from being simultaneously activated.

During monopolar operation of an electrosurgical device (not shown), a first electrode, often referred to as the active electrode, is provided with electrosurgical device to be used at a surgical site while a return electrode, which can be referred to as the indifferent or neutral electrode, is provided remote from the surgical site and often in the form of a ground pad dispersive electrode 32 located on a patient. For example, the pad dispersive electrode 32 is typically on the back, buttocks, upper leg, or other suitable anatomical location during surgery. In such a configuration, the pad dispersive electrode 32 is often referred to as a patient return electrode. An electrical circuit of RF energy is formed between the active electrode and the pad dispersive electrode 32 through the patient.

During bipolar operation of electrosurgical device 30 as illustrated, an active electrode providing the first electrical pole and another electrode, often referred to as the return electrode providing a second electrical pole, is provided at the surgical site, such as part of the device 30. An electrical circuit of RF energy is created between the first and second poles of the device 30. Historically, the pad dispersive electrode 32 was not used in bipolar operation. In the present example of bipolar operation of electrosurgical device 30, however, a second return electrode, which applied to the patient in a region typically remote from the surgical site, such as the dispersive electrode 32, is used in during bipolar operation of electrosurgical device 30. Both the second return electrode, such as the dispersive electrode 32, and the return electrode on the surgical device 30, i.e., a first return electrode, are coupled together and to a measurement circuit in the electrosurgical unit 10. A significant portion of the current may not flow through the patient's body to the second return electrode, such as the pad dispersive electrode 32 as in a the monopolar mode, but rather through a localized portion of tissue between the poles of the device 30, i.e., the active and first return electrodes.

The electrosurgical device 30 in the example is connected to electrosurgical unit 10 via cable 24. Cable 24 includes plugs 34 that connect with receptacles 36 on the electrosurgical unit 10. In one example, a receptacle can correspond with an active electrode receptacle and one or more receptacles can correspond with controls on the electrosurgical device 30. Still further, a receptacle can correspond with a second active electrode receptacle. An additional cable may connect the pad dispersive electrode 32 to a pad receptacle of the electrosurgical unit 10. In some examples, delivery tubing 16 and cable 24 are combined to form a single cable 26.

In one example, the electrosurgical unit 10 is capable of operating in at least bipolar mode with a connection for a second return electrode, such as for the pad dispersive electrode. In another example, the electrosurgical unit 10 is cable of operating in both a bipolar mode and a monopolar mode. In still another example, the electrosurgical unit 10 is capable of operating in monopolar and bipolar modes as well as multiple functions with a mode such as a monopolar cutting function, a monopolar coagulation function, and monopolar hemostasis or tissue sealing function as well as at least a bipolar hemostasis or tissue sealing function. For example, monopolar RF energy is provided to the device 30 at a first power level and/or a first waveform (collectively first, or cutting RF energy setting) for the monopolar cutting function. Cutting RF energy for a cut function may be provided at a relatively low voltage and a continuous current (100% on, or 100% duty cycle). Nominal impedance can range between 300 to 1000 ohms for the cutting function. At a power setting of 90 Watts for cutting, voltage can range from approximately 164 to 300 volts root mean square (RMS). In the monopolar coagulation function, monopolar RF is energy is provided to the electrode at a second power level and/or second waveform (collectively second, or coagulating RF energy setting) that is different than at least one of the first power level or the first waveform. For example, coagulating RF energy for a coagulation function may be provided at a relatively higher voltage than the cut voltage and with a pulsed current, such as 1% to 6% on and 99% to 94% off, respectively (or 1% to 6% duty cycle). Other duty cycles are contemplated.

The electrosurgical unit 10 may provide bipolar RF energy at a third power level and/or third waveform (collectively third, or hemostatic sealing RF energy setting) along with fluid for a (generally low voltage) hemostasis or tissue sealing function that may be the same as or different than the cutting and coagulating RF settings provided to the device 30 for the cut function or the coagulation function. In one example, hemostatic sealing energy can be provided with a continuous current (100% duty cycle). Nominal impedance can range between 100 to 400 ohms for the hemostatic sealing function. At a power setting of 90 Watts for hemostatic sealing, voltage can range from approximately 95 to 200 volts RMS.

In one example, the electrosurgical unit 10 provides RF energy to the active electrode as a signal having a frequency in the range of 100 KHz to 10 MHz. Typically this energy is applied in the form of bursts of pulses. Each burst typically has a duration in the range of 10 microseconds to 1 millisecond. The individual pulses in each burst typically each have a duration of 0.1 to 10 microseconds with an interval between pulses of 0.1 to 10 microseconds. The actual pulses are often sinusoidal or square waves and bi-phasic, that is alternating positive and negative amplitudes.

The electrosurgical unit 10 includes a power switch to turn the unit on and off and an RF power setting display to display the RF power supplied to the electrosurgical device 30. The power setting display can display the RF power setting numerically in a selected unit such as watts.

The example electrosurgical unit 10 includes an RF power selector comprising RF power setting switches that are used to select or adjust the RF power setting. A user can push one power setting switch to increase the RF power setting and push the other power setting switch to decrease the RF power setting. In one example, power setting switches are membrane switches, soft keys, or as part of a touchscreen. In another example, the electrosurgical unit may include more than one power selectors such as a power selector corresponding with each of the different monopolar settings used in the different functions.

The example electrosurgical unit 10 can also include fluid flow rate setting display and flow rate setting selector. The display can include indicator lights, and the flow rate selector can include switches. Pushing one of the flow rate switches selects a fluid flow rate, which is than indicated in display.

Electrosurgical unit 10 can be configured to include control of the pump 22. In this example, the speed of the pump 22, and the fluid throughput, can be predetermined based on input variables such as the RF power setting and the fluid flow rate setting. In one example, the pump 22 can be integrated with the electrosurgical unit 10.

Figure 2:
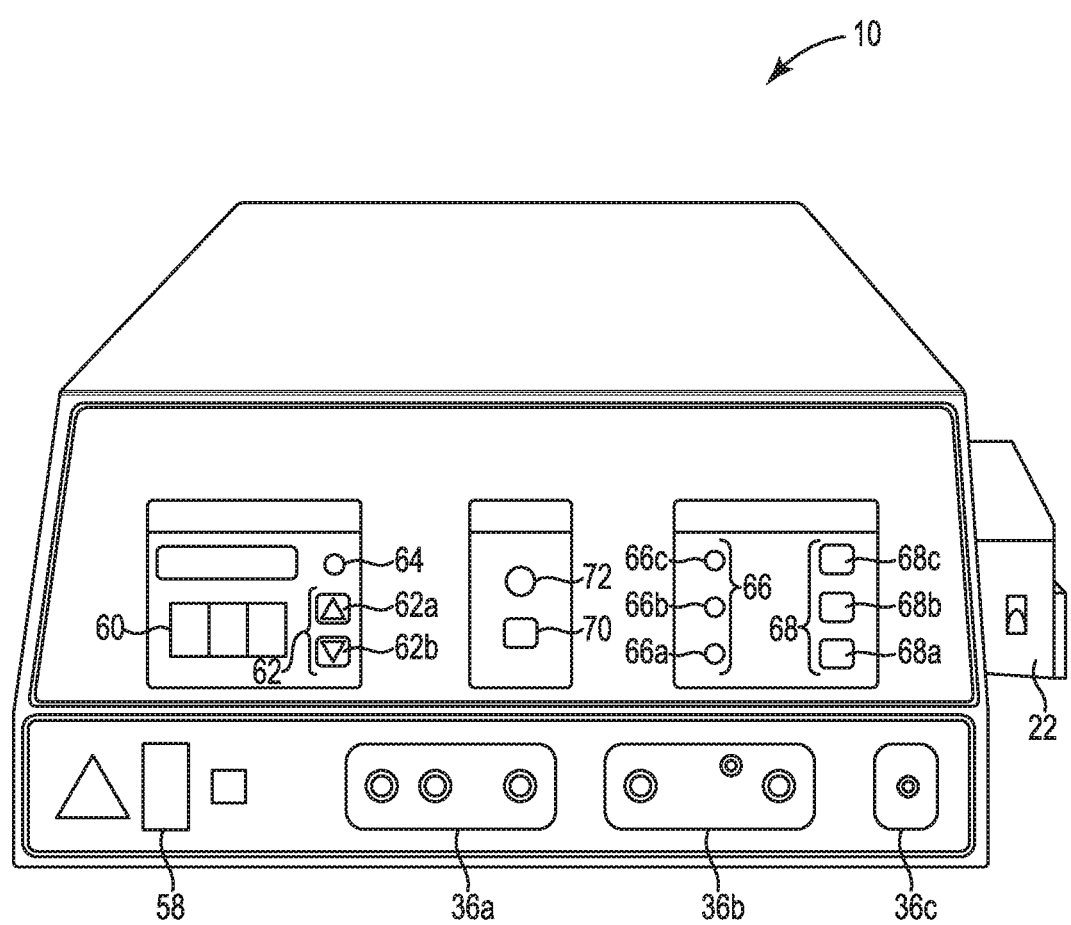
FIG. 2 is a front view illustrating the example electrosurgical unit of FIG. 1.

FIG. 2 illustrates an example front panel of electrosurgical unit 10. A power switch 58 can be used to turn the electrosurgical unit 10 on and off. After turning the electrosurgical unit 10 on, an RF power setting display 60 may be used to display the RF power setting numerically in watts. The power setting display 60 may further comprise a liquid crystal display (LCD).

Electrosurgical unit 10 may further comprise an RF power selector 62 comprising RF power setting switches 62a, 62b that may be used to select the RF power setting. Pushing the switch 62a may increase the RF power setting, while pushing the switch 62b may decrease the RF power setting. RF power output may be set in five-watt increments in the range of 20 to 100 watts, and ten-watt increments in the range of 100 to 200 watts. Additionally, electrosurgical unit 10 may include an RF power activation display 64 comprising an indicator light that can illuminate when RF power is activated, either via a hand switch on electrosurgical device 30 or a footswitch. Switches 62a, 62b comprise membrane switches. While only one RF power selector 62 is shown, electrosurgical unit 10 can have multiple such RF power selectors such as one each for monopolar and bipolar power selection.

The example electrosurgical unit 10 can also include fluid flow rate setting display and flow rate setting selector. The display can include indicator lights, and the flow rate selector can include switches. Pushing one of the flow rate switches selects a fluid flow rate, which is than indicated in display.

Electrosurgical unit 10 can further include a fluid flow rate setting display 66. Flow rate setting display 66 may comprise three indicator lights 66a, 66b and 66c with first light 66a corresponding to a fluid flow rate setting of low, second light 66b corresponding to a fluid flow rate setting of medium (intermediate) and third light 66c corresponding to a flow rate setting of high. One of these three indicator lights will illuminate when a fluid flow rate setting is selected.

Electrosurgical unit 10 can further include a fluid flow selector 68 comprising flow rate setting switches 68a, 68b and 68c used to select or switch the flow rate setting. Three push switches may be provided with first switch 68a corresponding to the fluid flow rate setting of low, second switch 68b corresponding to a fluid flow rate setting of medium (intermediate) and third switch 68c corresponding to a flow rate setting of high. Pushing one of these three switches may select the corresponding flow rate setting of low, medium (intermediate) or high. The medium, or intermediate, flow rate setting may be automatically selected as the default setting if no setting is manually selected. Switches 68a, 68b and 68c may comprise membrane switches.

Before starting a surgical procedure, it may be desirable to prime device 30 with fluid 12. Priming may be desirable to inhibit RF power activation without the presence of fluid 12. A priming switch 70 may be used to initiate priming of device 30 with fluid 12. Pushing switch 70 once may initiate operation of pump 22 for a predetermined time period to prime device 30. After the time period is complete, the pump 22 may shut off automatically. When priming of device 30 is initiated, a priming display 72 comprising an indicator light may illuminate during the priming cycle.

While not being bound to a particular theory, the relationship between the variables of fluid flow rate Q (such as in units of cubic centimeters per minute (cc/min)) and RF power setting $P_S$ (such as in units of watts) can be configured to inhibit undesired effects such as tissue desiccation, electrode sticking, smoke production, char formation, and other effects while not providing a fluid flow rate Q at a corresponding RF power setting $P_S$ not so great as to disperse too much electricity and or overly cool the tissue at the electrode/tissue interface. Electrosurgical unit 10 is configured to increase the fluid flow rate Q generally linearly with an increasing RF power setting $P_S$ for each of the three fluid flow rate settings of low, medium, and high.

Electrosurgical unit 10 includes a set of receptacles 36 coupled to circuitry and configured to receive cables. Receptacles 36 can includes bipolar power output receptacles 36a, monopolar power output receptacles 36b, and pad dispersive electrode receptacle 36c. The bipolar power output receptacles 36a can include an electrical connector configured to receive, for example, male banana plug connectors attached to conductors operably coupled to a bipolar electrosurgical device or bipolar elements of a multifunction electrosurgical device. In one example, the electrosurgical unit 10 includes three bipolar power output receptacles 36a. In one example, the bipolar power output receptacles 36a include an active electrode receptacle to be electrically coupled to an active electrode on the electrosurgical device 30, a return electrode receptacle to be electrically coupled to a return electrode on the electrosurgical device 30, and a controller receptacle to provide control signals to the turn on and turn off the electrosurgical device. In some examples, the bipolar output receptacle can include one or more additional return electrical receptacles suitable for connecting to at least a second return electrode for use with the electrosurgical device in the bipolar mode. The monopolar power out receptacles 36b can be configured to receive conductors operably coupled to a monopolar electrosurgical device or monopolar elements of a multifunction electrosurgical device. The pad dispersive electrode receptacle 36c can include a connector to receive a conductor operably coupled to the pad dispersive electrode 32. In the example, the pad dispersive electrode receptacle 36c and some or all of the bipolar output receptacles 36a are coupled to detection circuits within the electrosurgical unit 10.

In some examples, the electrosurgical unit 10 can include a display or a data output couplable to an external monitor to provide graphical or indications of impedance of tissue between electrodes of the electrosurgical device 30 and pad dispersive electrode 32 as determined by the measurement circuits coupled to receptacles 36a, 36c.

Figure 3:
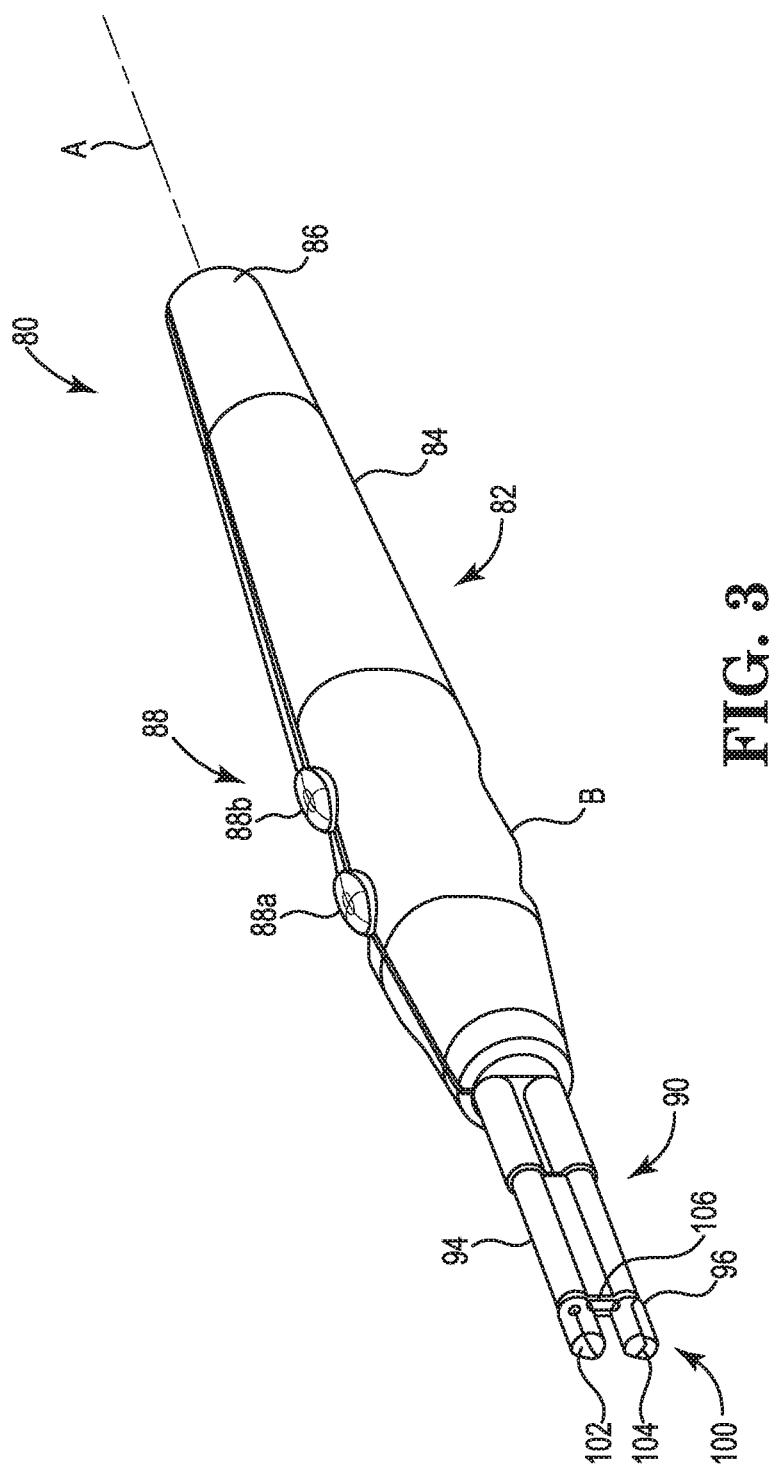
FIG. 3 is a perspective view illustrating an example of the electrosurgical device of FIG. 1 including a bipolar electrode assembly.

FIG. 3 illustrates an example of an electrosurgical device 80, which can correspond with electrosurgical device 30, having at least a bipolar electrode assembly 100 that that can be used in conjunction with electrosurgical unit 10 and pad dispersive electrode 32. Bipolar electrode assembly 100 includes distally extending electrodes 102, 104 having exposed conductive surfaces configured to be electrically coupled to a source of bipolar RF energy supplied from electrosurgical unit 10 as well as to measurement circuitry in electrosurgical unit 10. Electrode assembly 100 can be further configured as an active electrode 102 and return electrode 104 for the purposes of illustration. In one example, electrodes 102, 104 are in a co-planar arrangement to provide for a robust electrode/tissue interface. Electrodes 102, 104 may be formed to optimize hemostatic sealing of bone and tissue or coagulation in conjunction with delivery of fluid or for a particular application or anatomical geometry.

Electrosurgical device 80 extending along longitudinal axis A includes a handpiece 82. Handpiece 82 includes a handle 84 that can include a finger grip portion with ridges shown on the lower surface or bottom B of the device 80 and intended to be held in the surgeon's hand. The handpiece 82 includes a proximal end 86 for balance and, in the example, includes an electrical connector for electrically coupling cable 24 to the device 80.

Handpiece 82 may be configured to enable a user of electrosurgical device 80 to hold and manipulate device 80 between the thumb and index finger like a writing instrument or an electrosurgical pen. Handpiece 82 may comprise a sterilizable, rigid, electrically insulative material, such as a synthetic polymer (e.g., polycarbonate, acrylonitrile-butadiene-styrene). The handle 84 can include an upper surface, or top T, opposite bottom B. A controller 88, such as a set of one or more switches coupled to circuitry such as on a printed circuit board, in the example is disposed on top T and configured to be operated by the user's thumb or index finger to activate the electrode assembly 100.

The electrosurgical device 80 can include a probe assembly 90 extending distally from the handpiece 82. The probe assembly 90 in the example includes a shaft 94. The shaft 94, or other portions of electrosurgical device 80 may include one or more elements forming a subassembly to be generally one or more of rigid, bendable, fixed-length, variable-length (including telescoping or having an axially-extendable or axially-retractable length) or other configuration.

In one example, the handle 84 and shaft 94 can be formed from an insulative material such as a high temperature micromolded polymer. Examples insulative materials can include polytetrafluoroethylene (PTFE), polycarbonate (PC), polyoxymethylene (POM or acetal), or polyether ether ketone (PEEK).

The shaft 94 carries one or more electrical conductors to a distal end 96 including the electrode assembly 100. Electrical pathways within the handpiece 80 and probe assembly 90 can be formed as conductive arms, wires, traces, other conductive elements, and other electrical pathways formed from electrically conductive material such as metal and may comprise stainless steel, titanium, gold, silver, platinum or any other suitable material. In the example, the shaft 94 includes a fluid lumen extending into the handpiece 82 for fluidly coupling to delivery tubing 16 in cable 26. The fluid lumen includes an outlet port 106 disposed on the electrode assembly 100 for selectively dispersing fluid 12. In one example, fluid lumen can be included in a hypotube configured to mate with delivery tubing 16 to supply fluid 12 to electrode assembly 100. Hypotube can be constructed from non-conductive commonly used flexible tubing, such as polyvinyl chloride (PVC), PEEK, or a thermoplastic elastomer (TPE). In one example, the TPE is a polyether block amide (PEBA) available under the trade designation PEBAX from Arkema of Colombes, France.

In one example, the controller 88 includes one or more pushbuttons 88a, 88b on the handle 82 in combination with circuitry such as a printed circuit board within the handle 82 to provide binary activation (on/off) control for each function of the electrosurgical device 80. For example, one button 88a may be pressed to selectively activate the electrode assembly 100 and disperse fluid from port 106 in a sealing function and disperse fluid 12. Alternate configurations of the controller 88 and its activation are contemplated.

In some examples, the electrosurgical devices 30, 80 may be used in other systems or the electrosurgical unit 10 may be used with other electrosurgical devices. Other examples of electrosurgical device 30 can include bipolar electrodes mounted on jaws or clamps that are movable with respect to each other. For example, jaws or clamps can selectively pinch tissue between the bipolar electrodes. Still further examples can include any suitable configuration of active and return electrodes at the treatment site. While the electrosurgical devices 30, 80 are described with reference to electrosurgical unit 10 and other elements of system 40, the description of the combination is for the purposes of illustrating system 40.

Figure 4:
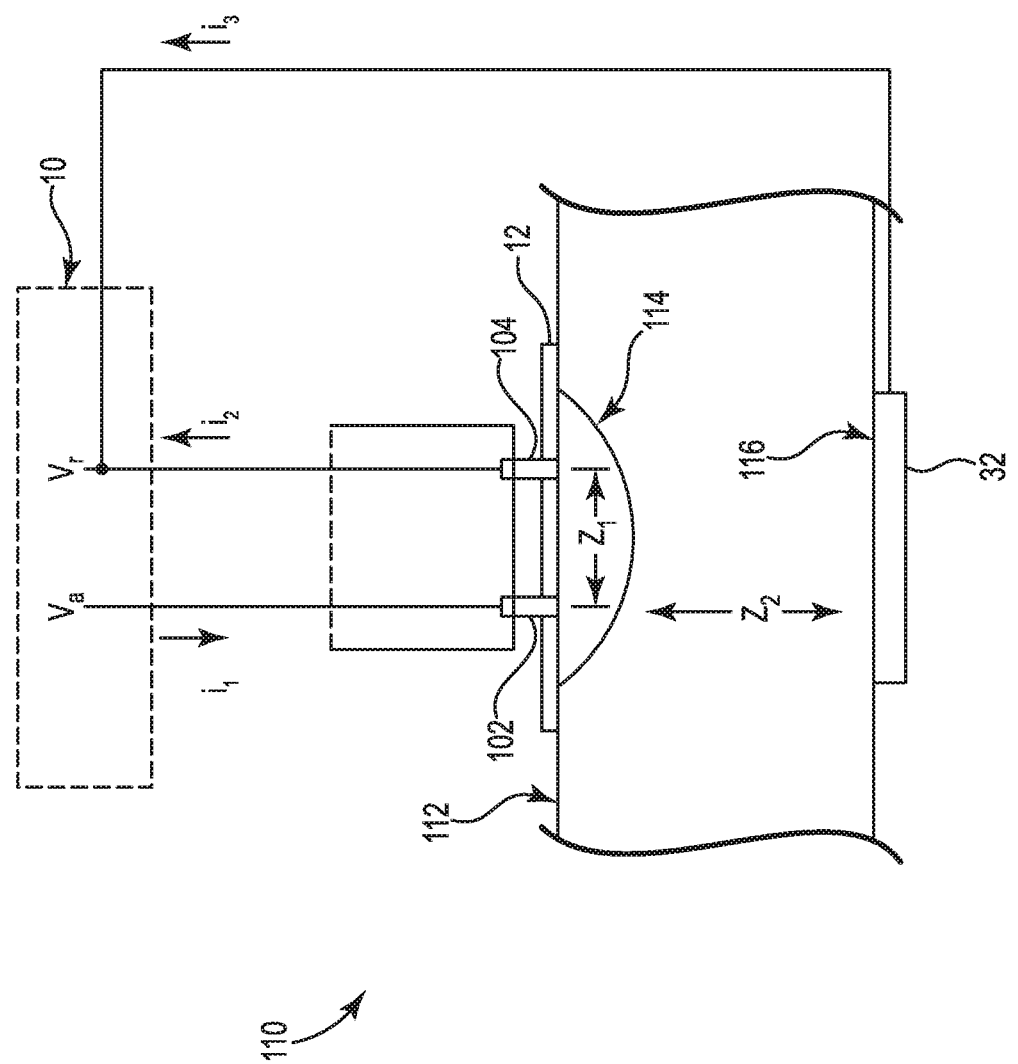
FIG. 4 is a schematic view of an environment including the electrosurgical system of FIG. 1 treating tissue.

FIG. 4 illustrates an environment 110 that exemplifies a method of system 40 including an example electrosurgical device 80 with a remote second return electrode such as pad dispersive electrode 32 operably coupled to electrosurgical unit 10. Environment 110 includes tissue 112 subjected to bipolar treatment from electrosurgical device 80 having active electrode 102 and return electrode 104 in the presence of fluid 12 at a tissue treatment site 114, such as a surgical site. During bipolar operation of the electrosurgical device 80, the electrosurgical unit 10 provides an RF signal to the active electrode 102 at an active voltage $V_a$ and an active current $i_1$ to the active electrode 102 at the treatment site 114. The electrosurgical unit 10 receives a return voltage $V_r$ and a first return current $i_2$ from the return electrode 104. A remote return electrode, such as a pad dispersive electrode 32 is operably coupled to the tissue 112 at remote site 116 remote from the treatment site 114 and provides a second return current $i_3$ to electrosurgical unit 10. In the example, the remote electrode, or pad dispersive electrode 32, is also at voltage $V_r$. The example treatment site 114 is in the presence of a fluid 12 provided by the electrosurgical device 80. In one example, the remote site 116 is not in the presence of the fluid 12 provided by the electrosurgical device 80. Impedance of the tissue 112, or $Z_1$ in the fluid 12 at the treatment site 114 can be determined as the voltage difference between the active electrode 102 and the return electrode 104 divided by the first return current, or $Z_1=(V_a-V_r)/i_2$. Impedance of the tissue 112, or $Z_2$ between active electrode 102 and the remote electrode, or pad dispersive electrode 32, at the remote site 116 can be determined as the voltage difference between the active electrode 102 and the remote electrode divided by the second return current, or $Z_2=(V_a-V_r)/i_3$. The electrosurgical unit 10 is configured to receive electrical signals from environment 110 and calculate the change in impedances $Z_1$ and $Z_2$ to determine when to adjust power to the active electrode 102.

Figure 5:
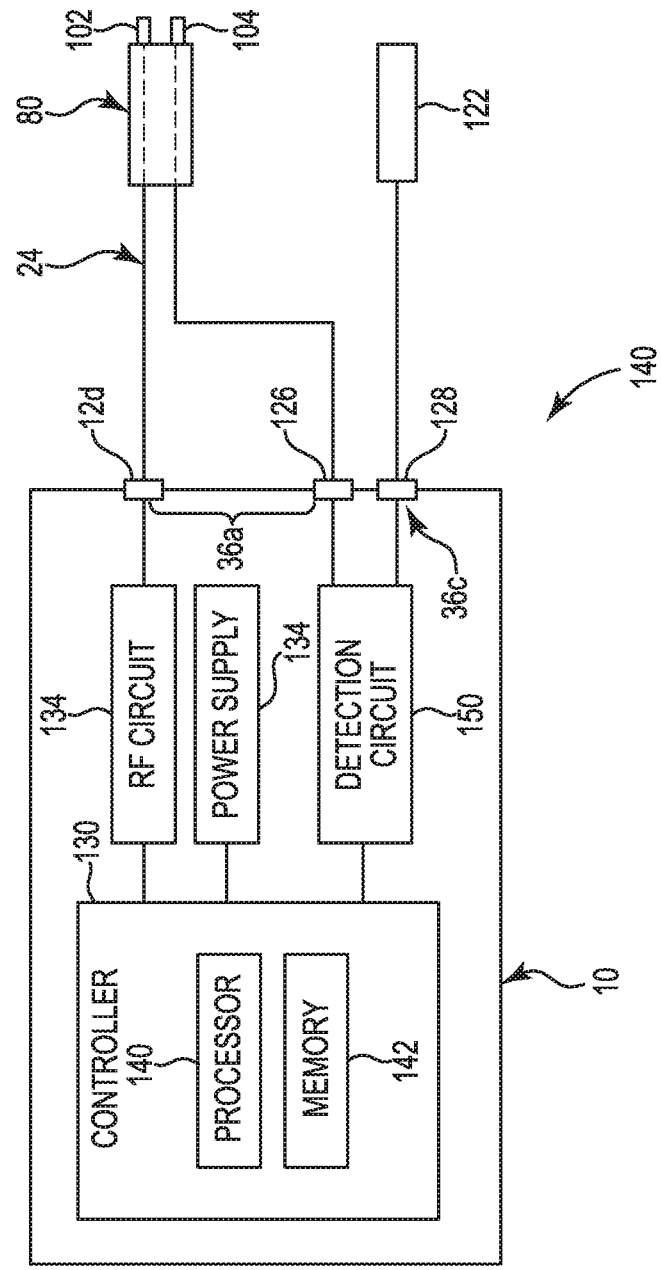
FIG. 5 is a schematic view illustrating example features of the electrosurgical unit in the system of FIG. 1.

FIG. 5 illustrates the system 40 including the electrosurgical unit 10 coupled to an example electrosurgical device 80 configured for a bipolar operation having an active electrode 102 and first return electrode 104 and also to a second, or remote, return electrode 122, such as a pad dispersive electrode 32. The electrosurgical unit 10 includes an active connection 124 that is configured to be electrically coupled to the active electrode 102, a first return connection 126 that is configured to be electrically coupled to the first return electrode 104, and a second return connection 128 that is configured to be coupled to the second return electrode 122. In one example, the active electrode connection 124 and first return connection 126 can be included as part of the receptacles 36 such as the bipolar output receptacles 36a. In this example, the second return connection 128 can be included as part of the receptacles 36 such as a second return electrode receptacle on the bipolar output receptacles 36a or the pad dispersive receptacle 36c. Other configurations are contemplated including the second return connection 128 having a receptacle that is separate from the pad dispersive receptacle 36c and the second return connection 128 being included as part of the bipolar output receptacles 36a.

The example electrosurgical unit 10 can include a controller 130, a high voltage power supply 132, and an RF output circuit 134. The power supply 132 provides high voltage power to the RF output circuit 134, which converts high voltage power, for example from a direct current, into RF energy and delivers the RF energy to the active connection 124. The RF output circuit 134 is configured to generate a plurality of waveforms having various duty cycles, peak voltages, crest factors, and other suitable parameters. Further, the controller 130 can be configured to cause operation of the pump, such as pump 22, to deliver a fluid during bipolar operation (not indicated)

The controller 130 in the example can include a processor 140 operably connected to a memory device 142. Examples of a memory device 142 can include a non-volatile memory device such as a read only memory (ROM), electronically programmable read only memory (EPROM), flash memory, non-volatile random access memory (NRAM) or other memory device, and a volatile memory device such as random access memory (RAM) or other memory device. Memory device 142 can include various combinations of one or both of non-volatile memory devices and volatile memory devices. The processor 140 includes an output port that is operably connected to the power supply 132, the RF output circuit 134, or both that allows the processor 140 to control the output of the electrosurgical unit 10 according to a selected scheme. In some examples, the processor 140 may include a microprocessor or a logic processor or other control circuit.

Any combination of hardware and programming may be used to implement the functionalities of the electrosurgical unit 10. Such combinations of hardware and programming may be implemented in a number of different ways. For example, the programming for the electrosurgical unit 10 may be processor executable instructions stored on at least one non-transitory machine-readable storage medium, such as memory device 142 and the hardware may include at least one processing resource, such as processor 140, to execute those instructions. In some examples, the hardware may also include other electronic circuitry to at least partially implement at least one feature of electrosurgical unit 10. In some examples, the at least one machine-readable storage medium, such as a memory device 142, may store instructions that, when executed by the processor 140, at least partially implement some or all features of electrosurgical unit 10 and. In such examples, electrosurgical unit 10 may include the at least one machine-readable storage medium storing the instructions and the at least one processing resource to execute a method. The processor-executable instructions may be in the form of an application, such as a computer application or module of a computer application. In other examples, the functionalities of electrosurgical unit 10 and method may be at least partially implemented in the form of electronic circuitry.

The electrosurgical unit 10 also includes a detection circuit 150 electrically coupled to the first return connection 126, second return connection 128, and operably coupled to the controller 130. In one example, the detection circuit 150 can be operably coupled to the active connection 124 or receive signals indicative of the voltages or currents provided to the active electrode 102. The features and functions described below as included in the detection circuits such as detection circuit 150, in this disclosure may be, in some examples, included in or performed with the controller 130, vice versa, or some other combination. Furthermore, features and functionality of the detection circuit 150 can be implemented from one or more of conductors, circuit elements such as relays, hardware, and software. For example, the detection circuit 150 can include circuit elements or paths operably coupled to the RF circuit 134 or at least some of the bipolar receptacles 36a and the pad dispersive receptacles 36c that are configured to provide a signal representative of the active and return voltages and return currents. The circuit elements can include current probes to measure currents of interest. The circuit elements can be provided to an analog to digital converter that is then configured to provide digital signals to the controller 130.

In the example, the detection circuit 150 is able to detect at least the return voltage or voltages, such as $V_r$, at the first return electrode 102 and the second return electrode 122, and can also be configured to detect the first and second return currents $i_2$ and $i_3$ provided from the first return electrode 104 and second return electrode 122. The controller 130 also receives a signal indicating the active voltage $V_a$ at the active electrode 102 and the active current $i_1$ provided from the active connection 124 to the active electrode 102. The detection circuit 150 and controller 130 operate together to determine the impedances or impedances over time in the tissue forming an electrical path between the active electrode 102 and the first return electrode 104 at the treatment site 114 and in the tissue forming the electrical path between the active electrode 102 and the second return electrode 122 at the remote site 116 while treating tissue 112 during surgery. For example, controller 130 can receive a signal representative of the voltages at the active electrode 102 and the return electrode 104 and the first return current $i_2$, to calculate an impedance at the treatment site 114 or $Z_1=(V_a-V_r)/i_2$ and a signal representative of the voltages at the active electrode 102 and the remote electrode 122 and the second return current $i_3$, to calculate an impedance at the remote site 116, or $Z_2=(V_a-V_r)/i_3$.

The illustrated examples contemplate that the voltage value at the first return electrode is set to the voltage value at the second return electrode, or $V_r$. In other examples, the detection circuit 150 may provide independent voltage values for the voltages at the first return electrode and the second return electrode that may or may not be equal to each other. In still other examples, the electrosurgical unit may receive more than two return currents or return voltages from ore than two return electrodes and determine two or more impedance measurements at sites remote from the treatment site 112. Still other examples are contemplated.

In one example, controller 130 can include features to present the impedance measurement over time as a visualization to a display or screen as a graph, chart, numerical value, or other visual indication. In another example, the controller 130 can include an indicator device to provide an audio indication or visual indication, such as an alarm sound or lights, upon a selected condition of the impedance measurements or the impedance measurement at the remote site 116. The impedance measurement indicative of a selected condition, in one example, can be related impedance of the tissue at the remote site 116 if the impedance of the tissue at the treatment site 114 is noisy or determined to be of secondary importance to the impedance of the tissue at the treatment site 114. Other selected conditions of interest may be detected via the impedance measurements. A clinician can receive an indication that an impedance threshold representative of the selected condition has been reached, and selectively adjust the RF energy to the active electrode 84, i.e., such as reduce or cut power, or take other action accordingly. Still further, the controller 130 can include a component to automatically adjust power or signals to the active electrode 102 of the electrosurgical device upon detection of a selected condition via the impedance measurement.

Figure 6:
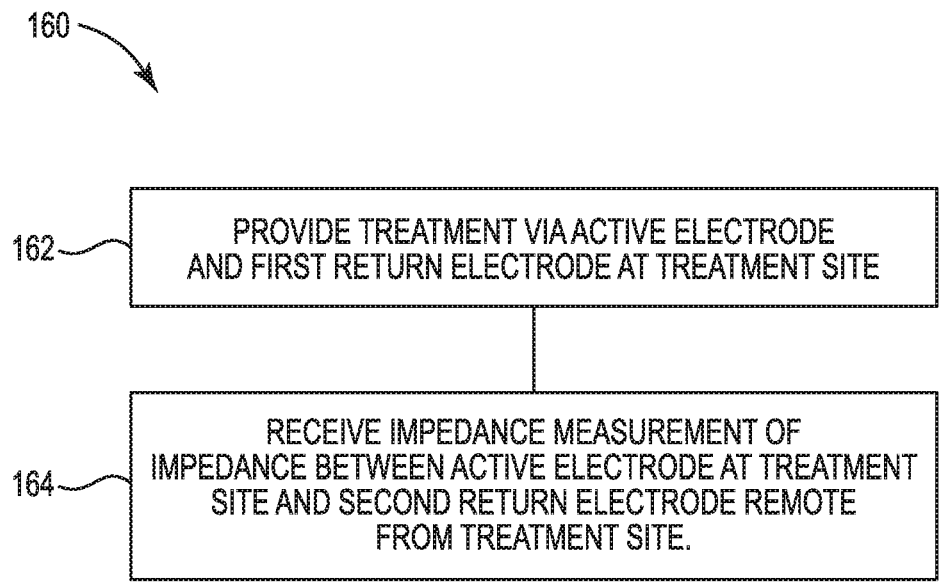
FIG. 6 is a block diagram illustrating an example method that can be used with the electrosurgical system of FIG. 1 in the example environment of FIG. 4 such as with the example electrosurgical unit of FIG. 5.

FIG. 6 illustrates an example method 160 for use with the electrosurgical system 40 including the electrosurgical unit 10. Electrosurgical treatment with an RF energy is provided to tissue 112 via an active electrode, such as active electrode 102 at a treatment site, such as treatment site 114, and a first return electrode, such as first return electrode 104, at the treatment site at 162. In this example, the active electrode and first return electrode are configured for bipolar operation. An electrical circuit of RF energy is created between the active electrode and the first return electrode at the treatment site 114. Further, the RF energy can be provided in the presence of a fluid, such as fluid 12, at the treatment site 114. During the electrosurgical treatment an impedance measurement is determined in the tissue 112 between the active electrode at the treatment site and a second return electrode, such as second return electrode 122 or pad dispersive electrode 32, disposed remote from the treatment site such as at remote site 116 at 174. As indicated in the example electrosurgical unit 10, the controller 130 can receive signals representative of voltages and currents from detection circuit 150 and determine the impedance in the tissue 112 at the remote site 116 via $Z_2=(V_a-V_r)/i_3$. The electrosurgical treatment can be based on this impedance, such as selected parameters of this impedance including impedance over time, at 176. In one example, the controller 130 can cause the RF output circuit 134 to stop providing RF energy to the electrosurgical device 30 if the impedance has plateaued or other detected and selected feature of the impedance.

As described, impedance of tissue at the treatment site 114 will increase with thermal delivery as a function of time until the impedance reaches a plateau, at which point thermal delivery will no longer treat the tissue as intended, or ineffectively treat the tissue. When the impedance reaches the plateau, the impedance measurement as a function of time exhibits a characteristic that generally indicates further subjecting the tissue to RF energy at the power level will no longer provide effective treatment. In one example, a characteristic of an impedance plateau can include a general leveling off of the rate of change of impedance as a function of time, whereas during effective treatment the rate of change of impedance as a function of time may increase. In one illustrated example, the impedance plateau can be reached at approximately one second of thermal treatment. In some circumstances of bipolar treatment, however, the impedance plateau is difficult to detect with a bipolar electrosurgical device such as device 30 and historical electrosurgical units. For example, the presence of a conductive fluid 12 such as saline in the area of thermal delivery during hemostasis may add a parallel electrical load to the tissue 112 between the active electrode and the return electrode of the bipolar electrosurgical device. The parallel load in the presence of tissue can affect the impedance measurement in the form of electrical noise that can adversely affect the ability of the historical electrosurgical unit to determine whether to adjust power. In the illustrated example, an electrosurgical device that detects impedance in the tissue between the active and return electrodes on the electrosurgical device may not detect the impedance plateau until approximately 2.6 seconds, which is over twice as long after effective treatment has completed.

In the present example, using system 40 with electrosurgical unit 10 to provide a bipolar treatment with the presence of a conductive fluid 12, the impedance plateau may be detected significantly sooner. In the electrosurgical unit 10, the controller 130 can cause the RF output circuit 134 to adjust power to the electrosurgical device 30 upon detection of the impedance plateau as measured in the tissue between the active electrode 102 and the second return electrode 122 and provide for a more effective treatment.

Figure 7:
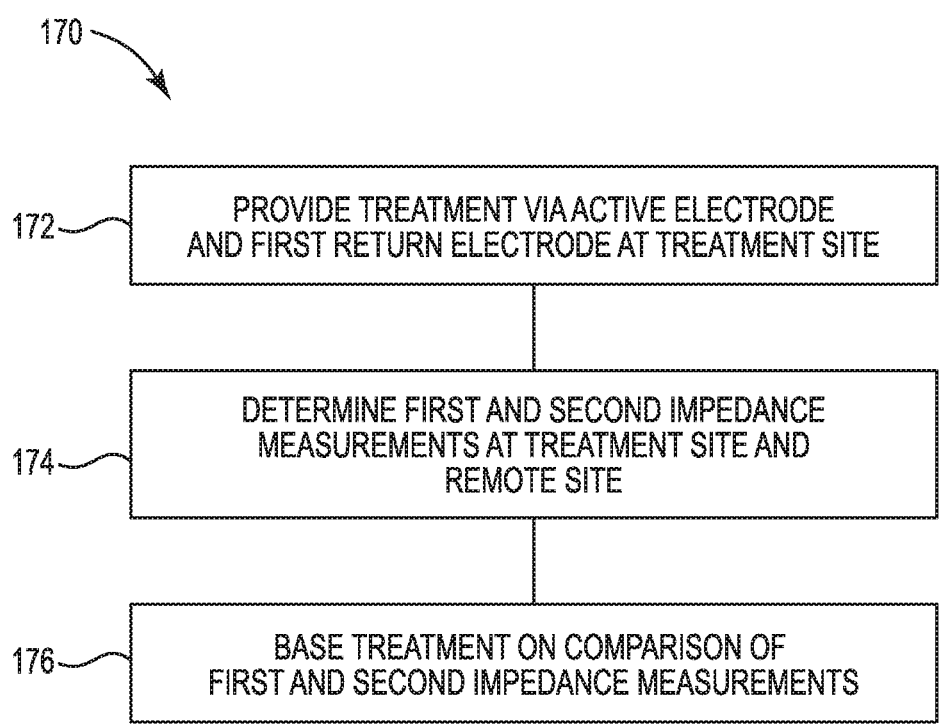
FIG. 7 is a block diagram illustrating another example method that can be used with the electrosurgical system of FIG. 1 in the example environment of FIG. 4 such as with the example electrosurgical unit of FIG. 5.

FIG. 7 illustrates an example method 170 for use with the electrosurgical system 40 including the electrosurgical unit 10. Electrosurgical treatment is provided to tissue 112 via an active electrode, such as active electrode 102 at a treatment site, such as treatment site 114, and a first return electrode, such as first return electrode 104, at the treatment site at 172. In this example, the active electrode and first return electrode are configured for bipolar operation. An electrical circuit of RF energy is created between the active electrode and the first return electrode at the treatment site 114. Further, the RF energy can be provided in the presence of a fluid, such as fluid 12, at the treatment site 114. During the electrosurgical treatment both a first impedance measurement is determined in the tissue between the active electrode at the treatment site and first return electrode at the treatment site and a second impedance measurement is determined in the tissue 112 between the active electrode at the treatment site and a second return electrode, such as second return electrode 122 or pad dispersive electrode 32, disposed remote from the treatment site such as at remote site 116 at 174. As indicated in the example electrosurgical unit 10, the controller 130 can receive signals representative of voltages and currents from detection circuit 150 and determine the first impedance in the tissue 112 at the treatment site 114 via $Z_1=(V_a-V_r)/i_2$ and the second impedance at the remote site 116 via $Z_2=(V_a-V_r)/i_3$.

The electrosurgical treatment can be based on a comparison of the first impedance to the second impedance, such as selected parameters of first and second impedance including impedance over time, at 176. For example, the treatment can be adjusted based on the comparison of the first and second impedance measurements. In one example, the controller 130 can cause the RF output circuit 134 to stop providing RF energy to the electrosurgical device 30 if the one or the other of the impedance measurements has plateaued or other detected and selected feature of the comparison of impedance at 176. In one example, a look up table of impedance characteristics can be stored in a memory device, such as memory device 142 and compared to the measured or detected impedances at 176. Power may be adjusted or cut off to the electrosurgical device 30 via controller 130 and RF output circuit 134 if, for example, the second impedance measurement over time has started to plateau and the first impedance measurement is noisy. In some examples, power may be adjusted or cutoff if the first impedance measurement over time has started to plateau but the second impedance measurement has not started to plateau. Other outputs from the controller 130 and electrosurgical device 10 may be provided based on various combinations of the characteristics of the first and second impedance measurements as determined in the comparison at 176.

The example methods 600, 700 can be implemented to include a combination of one or more hardware devices and computer programs for controlling a system, such as a electrosurgical unit 10 having a processor 140 and memory 142, to perform methods 600, 700 apply electrosurgical treatment to tissue 112 at a treatment site 114 and detect impedance in tissue 112 with a return electrode at a remote site 116. Methods 600, 700 can be implemented as a computer readable medium or computer readable device having set of executable instructions for controlling the processor to perform the method 100. In one example, computer storage medium, or non-transitory computer readable medium, includes RAM, ROM, EEPROM, flash memory or other memory technology, that can be used to store the desired information and that can be accessed by the computing system. Accordingly, a propagating signal by itself does not qualify as storage media. Computer readable medium may be located with the electrosurgical system 40, the electrosurgical unit 10 or on a computing device on network communicatively connected to the electrosurgical unit 10. Methods 600, 700 can be applied as computer program, or computer application implemented as a set of instructions stored in the memory, and the processor can be configured to execute the instructions to perform a specified task or series of tasks. In one example, the computer program can make use of functions either coded into the program itself or as part of library also stored in the memory.

Although the present disclosure has been described with reference to preferred embodiments, workers skilled in the art will recognize that changes can be made in form and detail without departing from the spirit and scope of the present disclosure.

What is claimed is:

1. A method for use with an active electrode and a plurality of return electrodes, the method comprising:
providing an electrosurgical treatment with a treatment signal to tissue via the active electrode at a treatment site and a first return electrode of the plurality of return electrodes, wherein the active electrode and the first return electrode are in bipolar operation at the treatment site; and
determining an impedance measurement of an impedance in the tissue between the active electrode at the treatment site and a second return electrode of the plurality of return electrodes, the second return electrode being at a site remote from the treatment site to receive the treatment signal, the impedance measurement determined from the treatment signal received at the second return electrode.

2. The method of claim 1 comprising adjusting the electrosurgical treatment via the active electrode based on the impedance measurement.

3. The method of claim 2 wherein the adjusting the electrosurgical treatment includes cutting power to the active electrode in response to a plateau in the impedance measurement.

4. The method of claim 3 wherein the plateau includes a leveling off of the rate of change of impedance as a function of time.

5. The method of claim 1 wherein providing the electrosurgical treatment includes providing a radio-frequency (RF) energy to the tissue.

6. The method of claim 5 wherein the providing the electrosurgical treatment includes operating the electrosurgical device in a bipolar mode.

7. The method of claim 5 wherein providing the electrosurgical treatment includes providing a fluid at the treatment site and not the remote site.

8. The method of claim 7 wherein providing the fluid includes providing a conductive fluid.

9. The method of claim 1 wherein the electrosurgical treatment includes a hemostatic sealing of the tissue.

10. The method of claim 1 wherein the electrosurgical device includes a bipolar sealer.

11. A method for use with an active electrode and a plurality of return electrodes, the method comprising:
providing an electrosurgical treatment with a treatment signal to tissue via the active electrode at a treatment site and a first return electrode of the plurality of return electrodes, wherein the active electrode and the first return electrode are in bipolar operation at the treatment site;
determining a first impedance measurement of an impedance in the tissue between the active electrode at the treatment site and the first return electrode at the treatment site, the first impedance measurement determined from the treatment signal received at the first return electrode;
determining a second impedance measurement of an impedance in the tissue between the active electrode at the treatment site and a second return electrode of the plurality of return electrodes, the second return electrode being at a site remote from the treatment site to receive the treatment signal, the second impedance measurement determined from the treatment signal received at the second return electrode; and adjusting the treatment based on a comparison of the first impedance measurement with the second impedance measurement.

12. The method of claim 11 wherein the comparison includes detecting an impedance plateau in the second impedance measurement.

13. The method of claim 12 wherein the comparison includes detecting an impedance plateau in the second measurement and not in the first impedance measurement.

14. The method of claim 13 wherein the first impedance measurement is noisy.

15. The method of claim 13 wherein the adjusting treatment includes cutting power to the electrosurgical device.

16. The method of claim 11 wherein the first return electrode and second return electrode are at a same potential.

17. The method of claim 16 wherein the second impedance measurement include a difference in potential between the active electrode and the second return electrode divided by a current in the second return electrode during the treatment.

18. The method of claim 17 wherein the second impedance measurement is an impedance as a function of time.

19. The method of claim 11 wherein the plurality of return electrodes are two return electrodes.

20. The method of claim 11 wherein the active electrode and the first remote electrode are included on a bipolar device configured to provide a fluid at the treatment site.

21. A non-transitory computer readable medium to store computer executable instructions to control a processor to:
provide an electrosurgical treatment with a treatment signal to tissue via an active electrode at a treatment site and a first return electrode of a plurality of return electrodes, wherein the active electrode and the first return electrode are in bipolar operation at the treatment site; and
determine an impedance measurement of an impedance in the tissue between the active electrode at the treatment site and a second return electrode of the plurality of return electrodes, the second return electrode being at a site remote from the treatment site to receive the treatment signal, the impedance measurement determined from the treatment signal received at the second return electrode.

22. The non-transitory computer readable medium of claim 21 wherein the impedance measurement includes a difference between electrical potentials measured in the active electrode and the second return electrode divided by a current received from the second return electrode.

23. The non-transitory computer readable medium of claim 22 wherein the electrical potential of the second return electrode is set as the same as an electrical potential of the first return electrode.

24. The non-transitory computer readable medium of claim 21 comprising providing a visualization of the impedance measurement.

25. A non-transitory computer readable medium to store computer executable instructions to control a processor to:
provide an electrosurgical treatment with a treatment signal to tissue via an active electrode at a treatment site and a first return electrode of a plurality of return electrodes, wherein the active electrode and the first return electrode are in bipolar operation at the treatment site;
determine a first impedance measurement of an impedance in the tissue between the active electrode at the treatment site and the first return electrode at the treatment site, the first impedance measurement determined from the treatment signal received at the first return electrode;
determine a second impedance measurement of an impedance in the tissue between the active electrode at the treatment site and a second return electrode of the plurality of return electrodes, the second return electrode being at a site remote from the treatment site to receive the treatment signal, the second impedance measurement determined from the treatment signal received at the second return electrode; and
adjust the treatment based on a comparison of the first impedance measurement with the second impedance measurement.

26. The non-transitory computer readable medium of claim 25 wherein the second impedance measurement includes a difference between electrical potentials measured in the active electrode and the second return electrode divided by a current received from the second return electrode.

27. The non-transitory computer readable medium of claim 26 wherein the first impedance measurement includes a difference between electrical potentials measured in the active electrode and the first return electrode divided by a current received from the first return electrode.

28. The non-transitory computer readable medium of claim 26 wherein the electrical potential of the second return electrode is set as the same as an electrical potential of the first return electrode.

29. The non-transitory computer readable medium of claim 25 comprising selectively cutting power to the active electrode upon a detection of a plateau in the second impedance measurement.

30. The non-transitory computer readable medium of claim 29 comprising selectively cutting power to the active electrode if a plateau in the first impedance measurement is not detected.

31. The non-transitory computer readable medium of claim 25 comprising providing an alert upon a detection of a plateau in the second impedance measurement.

32. The non-transitory computer readable medium of claim 31 comprising providing a visualization of the second impedance measurement.

33. The non-transitory computer readable medium of claim 32 wherein the visualization includes a graph on a display.

34. An electrosurgical unit for use with an active electrode and a plurality of return electrodes, the electrosurgical unit comprising:
a memory to store a set of instructions; and
a processor to execute the set of instructions to:
provide an electrosurgical treatment with a treatment signal to tissue via the active electrode at a treatment site and a first return electrode of the plurality of return electrodes, wherein the active electrode and the first return electrode are in bipolar operation at the treatment site; and
determine an impedance measurement of an impedance in the tissue between the active electrode at the treatment site and a second return electrode of the plurality of return electrodes, the second return electrode being at a site remote from the treatment site to receive the treatment signal, the impedance measurement determined from the treatment signal received at the second return electrode.

35. The electrosurgical unit of claim 34 wherein the impedance measurement includes a difference between electrical potentials measured in the active electrode and the second return electrode divided by a current received from the second return electrode determined with the processor.

36. The electrosurgical unit of claim 35 wherein the electrical potential of the second return electrode is set as the same as an electrical potential of the first return electrode with a detection circuit operably coupled to the processor.

37. The electrosurgical unit of claim 34 comprising providing a visualization of the impedance measurement on a display operably coupled to the processor.

38. An electrosurgical unit for use with an active electrode and a plurality of return electrodes, the electrosurgical unit comprising:
 a memory to store a set of instructions; and
 a processor to execute the set of instructions to:
  provide an electrosurgical treatment with a treatment signal to tissue via the active electrode at a treatment site and a first return electrode of the plurality of return electrodes, wherein the active electrode and the first return electrode are in bipolar operation at the treatment site;
  determine a first impedance measurement of an impedance in the tissue between the active electrode at the treatment site and the first return electrode at the treatment site, the first impedance measurement determined from the treatment signal received at the first return electrode;
  determine a second impedance measurement of an impedance in the tissue between the active electrode at the treatment site and a second return electrode of the plurality of return electrodes, the second return electrode being a site remote from the treatment site to receive the treatment signal, the second impedance measurement determined from the treatment signal received at the second return electrode; and
  adjust the treatment based on a comparison of the first impedance measurement with the second impedance measurement.

39. The electrosurgical unit of claim 38 wherein the second impedance measurement includes a difference between electrical potentials measured in the active electrode in a detection circuit and the second return electrode divided by a current received from the second return electrode at the detection circuit, the detection circuit operably coupled to the processor.

40. The electrosurgical unit of claim 39 wherein the first impedance measurement includes a difference between electrical potentials measured in the active electrode and the first return electrode in the detection circuit divided by a current received from the first return electrode at the detection circuit.

41. The electrosurgical unit of claim 39 wherein the electrical potential of the second return electrode is set as the same as an electrical potential of the first return electrode at a detection circuit at the detection circuit.

42. The electrosurgical unit of claim 38 comprising selectively cutting power to the active electrode upon a detection of a plateau in the second impedance measurement via a signal from the processor to an RF circuit.

43. The electrosurgical unit of claim 42 comprising selectively cutting power to the active electrode if a plateau in the first impedance measurement is not detected.

44. The electrosurgical unit of claim 38 comprising providing an alert upon a detection of a plateau in the second impedance measurement in response to a signal from the processor.

45. The electrosurgical unit of claim 44 comprising providing a visualization of the second impedance measurement in response to another signal from the processor.

46. The electrosurgical unit of claim 45 wherein the visualization includes a graph on a display operably coupled to the processor.

47. An electrosurgical unit configured to provide a treatment with a bipolar electrosurgical device at a treatment site, the bipolar electrosurgical device having an active electrode and a first return electrode at the treatment site, and a second return electrode at a remote site, comprising:
 an RF circuit operably coupled to an output having an active electrode connection and a first return connection, the active electrode connection and the first return connection configured to be coupled to the bipolar electrosurgical device, the RF circuit configured to provide a bipolar operation of the bipolar electrosurgical device via the active electrode connection and the first return connection with a treatment signal;
 detection circuit configured to be operably coupled to the active electrode connection and the first return electrode connection, the detection circuit further configure to be operably coupled to a second return electrode connection, the second return electrode connection configured to be coupled to a second return electrode at a remote site; and
 a processor operably coupled to the detection circuit and configured to detect a potential difference from the treatment signal between the active electrode connection and the second return electrode connection and a current from on the treatment signal in the second return electrode connection, and to determine an impedance measurement based on the potential difference and the current during bipolar operation.

48. The electrosurgical unit of claim 47 wherein the processor is operably coupled to a display to provide a visualization of impedance in tissue over a period of time.

49. The electrosurgical unit of claim 47 comprising a fluid pump to selectively provide a conductive fluid during the bipolar operation.

50. An electrosurgical unit configured to provide a treatment with a bipolar electrosurgical device at a treatment site, the bipolar electrosurgical device having an active electrode and a first return electrode at the treatment site, and a second return electrode at a remote site, the electrosurgical unit comprising:
 a controller operably coupled to an RF circuit and configured to provide bipolar operation of the active electrode and the first return electrode with a treatment signal via the RF circuit;
 a detection circuit operably coupled to the controller, the detection circuit configured to receive an electrical potential from the second return electrode and current from the second return electrode;
 wherein the controller determines an impedance measurement of an impedance between the active electrode and the second return electrode during the treatment, the impedance measurement determined from the electrical potential from the second return electrode and the a current from the second return electrode from the treatment signal.

* * * * *